United States Patent [19]

Müllner et al.

[11] Patent Number: 5,707,840
[45] Date of Patent: Jan. 13, 1998

[54] MULTIFUNCTIONAL RNA HAVING SELF-PROCESSING ACTIVITY, THE PREPARATION THEREOF AND THE USE THEREOF

[75] Inventors: Hubert Müllner, Kelkheim; Eugen Uhlmann, Glashütten/Taunus; Peter Eckes; Rudolf Schneider, both of Kelkheim; Bernadus Uijtewaal, Heythuysen, all of Germany

[73] Assignee: Hoechst Aktiengesellschaft, Frankfurt am Main, Germany

[21] Appl. No.: 313,608

[22] Filed: Sep. 29, 1994

Related U.S. Application Data

[63] Continuation of Ser. No. 73,295, Jun. 7, 1993, abandoned, which is a continuation of Ser. No. 592,655, Oct. 4, 1990, abandoned.

[30] Foreign Application Priority Data

Oct. 6, 1989 [DE] Germany .................. 39 33 384.1

[51] Int. Cl.$^6$ .................. C12N 15/00; C12N 5/00; A01N 43/04; C07H 21/02
[52] U.S. Cl. .................. 435/172.1; 435/240.4; 435/252.3; 514/44; 536/23.1; 536/24.1; 935/33; 935/34; 935/44
[58] Field of Search .................. 435/252.3, 172.1, 435/240.4; 514/44; 536/23.1, 24.1; 935/33, 34, 44

[56] References Cited

U.S. PATENT DOCUMENTS 4,987,071 1/1991 Cech et al. .................. 435/91

FOREIGN PATENT DOCUMENTS 0321201 6/1989 European Pat. Off. .......... C12N 9/00
WO93/15194 8/1993 European Pat. Off. ......... C12N 15/11
89 05852 6/1989 WIPO.

OTHER PUBLICATIONS

Pamela Knight, Biocatalysts by Design, Bio-Technology 6:826–827 (Jul. 1988).
Chuat & Galibert, Can Ribozymes Be Used to Regulate Procaryote Gene Expression?, Biochemical and Biophysical Research Communications 162(3) :1025–1029 (Aug. 15, 1989).
Matt Cotten, The in vivo application of ribozymes, Tibtech 8:174–178 (Jul. 1990).
Rossi and Sarver, RNA enzymes (ribozymes) as antiviral therapeutic agents, Tibtech, 8:179–183 (Jul. 1990).
Chang et al., Ribozyme-Mediated Site-Specific Cleavage of the HIV-1 Genome, Clinical Biotechnology, 2(1):23–31 (Jan./Feb. 1990).
Evans et al., The effects of ribozymes on gene expression in plants, Biochemical Society Transactions 20:344S (1992).
Rezaian et al., Plant Molecular Biology 11:463–471 (1988).
Cuozzo et al., Biotechnology 6(5):549–557 (May 1988).
Forster et al. (1988), Nature vol. 334, pp. 265–267.
Walbot et al. (1988), Nature, vol. 334, pp. 196–197.

*Primary Examiner*—Mindy Fleisher
*Assistant Examiner*—Bonnie D. Weiss
*Attorney, Agent, or Firm*—Finnegan, Henderson, Farabow, Garrett & Dunner, L.L.P.

[57] ABSTRACT

A multifunctional RNA having self-processing activity, the preparation thereof and the use thereof.

Host cells can be transformed so that they express ribozyme RNA and antisense RNA which are connected with each other via a spacer. The RNA molecules can, for example, be complementary to a certain viral RNA. Plants which have been transformed with genes coding for RNA of this type show a significantly improved resistance to viruses.

10 Claims, 6 Drawing Sheets wherein

N   in the substrate-RNA are nucleotides of the substrate RNA, A, C, G or U N   in the ribozyme-RNA, starting at the 5' end, are as follows:

at positions 1-8 and 33-40, are complementary nucleotides to N in the substrate-RNA    at positions 13, 17, 18, 25 are variable nucleotides, A, C, G, or U, in the ribozyme    at positions 19-24 are variable nucleotides, A, C, G or U, in the loop of the ribozyme, wherein the number of the nucleotides can be 0-550.

Figure: 10 μg total DNA, digested with EcoRI, hybridized with entire fragment

1) λ PST           7) A-H6
2) Control         8) A-H7
3) A-H1            9) A-H9
4) A-H3           10) A-H10
5) A-H4           11) A-H12
6) A-H5           12) A-H15
                  13) A-H22

Fig. 6

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 479 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:1:

```
CCGGGAGGTA GCTCCTGATG AGTCCGTGAG GACGAAACAA CCTTGTCGTC GACAAAATGG      60

TCAGTATGCC CCTCGAGTGG TCTCCTTATG GAGAACCTGT GGAAAACCAC AGGCGGTACC     120

CGCACTCTTG GTAATATCAG TGTATTACCG TGCACGAGCT TCTCACGAAG CCCTTCCGAA     180

GAAATCTAGG AGATGATTTC AAGGGTAGCT CGACAACCTG GATCCAAAAT GGTCAGTATG     240

CCCCCCATGG CAACAGATTG GCGAATGAGA AAGTGGGTGG AGGACTTATC ATAGTAACAG     300

AAGAGAGACT AGAACTGCAG AAAATGGTCA GTATGCCCCA GATCTACCGG AGGTTCTACT     360

AGCATTGGGA GAGCTCGATT TGTCCATAGG CACACTGAGA CGCAAAAAGC TTAAGGTTGT     420

CGAGCTACCG GGGCCCAGGG CATACTCTGA TGAGTCCGTG AGGACGAAAC CATTTTGGG     479
```

( 2 ) INFORMATION FOR SEQ ID NO:2:

( i ) SEQUENCE CHARACTERISTICS:
        ( A ) LENGTH: 477 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:2:

```
CCCAAAATGG TTTCGTCCTC ACGGACTCAT CAGAGTATGC CCTGGGCCCC GGTAGCTCGA      60

CAACCTTAAG CTTTTTGCGT CTCAGTGTGC CTATGGACAA ACTGAGCTCT CCCAATGCTA     120

GTAGAACCTC CGGTAGATCT GGGCATACT GACCATTTTC TGCAGTTCTA GTCTCTCTTC      180

TGTTACTATG ATAAGTCCTC CACCCACTTT CTCATTCGCC AATCTGTTGC CATGGGGGGC     240

ATACTGACCA TTTTGGATCC AGGTTGTCGA GCTACCCTTG AAATCATCTC CTAGATTTCT     300

TCGGAAGGGC TTCGTGAGAA GCTCGTGCAC GGTAATACAC TGATATTACC AAGAGTGCGG     360

GTACCGCCTG TGGTTTTCCA CAGGTTCTCC ATAAGGAGAC CACTCGAGGG GCATACTGAC     420
```

```
CATTTTGTCG ACGACCAGGT TGTTTCGTCC TCACGGACTC ATCAGGAGCT ACCTCCC        477
```

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear     (ii) MOLECULE TYPE: RNA (genomic)

(ix) FEATURE:
        (A) NAME/KEY: misc_RNA
        (B) LOCATION: group(1..13, 17..30)
        (D) OTHER INFORMATION: /note= "n = nucleotides of the
            substrate RNA, A, C, G, or U"

(xi) SEQUENCE DESCRIPTION: SEQ ID NO:3:

```
NNNNNNNNN  NNNGUCNNNN  NNNNNNNNNN                                      30
```

(2) INFORMATION FOR SEQ ID NO:4:

(i) SEQUENCE CHARACTERISTICS:
        (A) LENGTH: 40 base pairs
        (B) TYPE: nucleic acid
        (C) STRANDEDNESS: single
        (D) TOPOLOGY: linear     (ii) MOLECULE TYPE: RNA (genomic)

(ix) FEATURE:
        (A) NAME/KEY: misc_feature
        (B) LOCATION: group(13, 17, 18, 25, 26)
        (D) OTHER INFORMATION: /note= "N = variable nucleotides,
            A, C, G, or U in the ribozyme."

(ix) FEATURE:
        (A) NAME/KEY: misc_feature
        (B) LOCATION: group(1..8, 33..40)
        (D) OTHER INFORMATION: /note= "N= complementary
            nucleotides to N in SEQ. ID. NO. 3 in the ribozyme."

(xi) SEQUENCE DESCRIPTION: SEQ ID NO:4:

```
NNNNNNNNCU  GANGAGNNNN  NNNNNNCGAA  ACNNNNNNNN                         40
```

MULTIFUNCTIONAL RNA HAVING SELF-PROCESSING ACTIVITY, THE PREPARATION THEREOF AND THE USE THEREOF

This application is a continuation of application Ser. No. 08/073,295 filed Jun. 7, 1993, now abandoned; which is a continuation of application Ser. No. 07/592,655, filed Oct. 4, 1990, abandoned.

RNA molecules can, under suitable conditions, catalyze reactions on other RNA molecules without the participation of proteins or autocatalytically cleave fragments of their own molecules. Thus an intron having 413 nucleotides is autocatalytically removed from the 3' end of the 23S rRNA of Tetrahymena thermophila and is transformed into a circular form. This takes place by a number of phosphoester transfer reactions with the participation of guanosine cofactors (Cech, T. R., Nature 30, 578–583 (1983)). Depending on the RNA substrate or the selected reaction conditions, the intron can function as a specific ribonuclease, terminal transferase, phosphotransferase or acid phosphatase. In this connection, an RNA molecule can carry out several reactions without itself being changed and, in this respect, behaves like an enzyme. For RNA molecules having these properties, the term ribozyme has therefore been introduced.

It has also been possible to show similar reactions without the participation of proteins for several viroid RNAs and satellite RNAs. Thus self-processing seems to be an essential reaction for the replication of Avocado Sunblotch Viroid (ASBV) (Hutchins, C. J. et al. Nucleic Acids Res. 14, 3627–3640 (1986)), satellite RNA from Tobacco Ringspot Virus (sTobRV) (Prody, G. A. et al, Science 231, 1577–1580 (1986)) and satellite RNA from Luzerne Transient Streak Virus (sLTSV) (Forster A. C. et al., Cell 49, 211–220 (1987)). Circular forms which, as templates, lead to the synthesis of extra long RNAs, are probably formed during the replication of these RNAs. These transcripts are cut to the appropriate length genome by the autocatalytic endonucleolytic reactions.

The structures of the RNAs which are presumably adopted by these for the reduction have been described as hammerheads (Forster A. C. et al., Cell 49, 211–220 (1987); Haseloff, J. et al., Nature 334, 585–591 (1988)).

The cleavage sites for these RNA enzymes are specific and must have certain structural preconditions in order to make processing possible.

It has now been found that host cells of any organism desired can be transformed using vectors which contain the DNA encoding ribozyme RNA coupled to antisense RNA so that the said DNA is expressed.

It is known that antisense RNA inhibits the gene expression in a number of procaryotic and eucaryotic cells, inter alia also in plant cells (Green, P. J. et al., Ann. Rev. Biochem. 55, 569 (1986)). Most of the mechanism of inhibition is still unclear. It is presumed that, in eucaryotic systems, double-stranded RNA is formed which hinders the transport of the mRNA to the cytoplasm.

Rezaian, M. et al. (Plant Mol. Biol. 11, 463 (1988)), for example, investigated the possibility of using antisense RNA as antiviral agent against Cucumber Mosaic Virus (CMV). However, the authors observed that the antiviral effectivity of the antisense RNA was unsatisfactory.

The coupling of the appropriate ribozyme RNA to the respective antisense RNA via a spacer effects now, for example, a more effective resistance to virus than could be shown by Rezaian however. Such a coupling of the RNA molecules thus in general effects an enhanced activity in transformed organisms which is directed against a substrate rather than only with respect to the activity as antiviral agent in plants.

The invention thus relates to
1. A gene coding for a ribozyme RNA sequence coupled to an antisense RNA sequence by a spacer.
2. Organisms which contain the gene specified under 1. or the corresponding RNA sequence.
3. The use of ribozyme RNA coupled to antisense RNA via a spacer as an agent in organisms which is directed against a substrate.

The invention is described in detail in the following, in particular in its preferred embodiments. The invention is furthermore defined in the claims.

The multifunctional RNA according to the invention is essentially composed such that the ribozymes are at the 3' and the 5' end of the RNA molecule in each case. Antisense RNA units are inserted in between via so-called spacers, which RNA units can likewise be connected with each other via spacers if there are several units. Preferred embodiments of the multifunctional RNA molecule can, shown in a pattern, be as follows:

5'-Ribozyme RNA-spacer-(antisense RNA)$_n$-spacer-ribozyme RNA-3' in which n is a number from 1 to 10, preferably 1 to 5, in particular 1 to 3. A chain of 20 to 25 nucleotides which, as a whole or in a part comprising at least 8, preferably 10–20 nucleotides, is complementary to the sequence of the ribozyme is inserted as spacer. The ribozyme sequence of the RNA can in this way associate with the spacer and cut the latter immediately behind a recognition sequence. If the number n is greater than 1, a spacer of this kind having a ribozyme cleavage site is likewise inserted between the respective antisense RNA molecules. A GUC cleavage site is preferably incorporated as ribozyme cleavage site. The antisense RNA can be directed against substrates, such as for example RNA coding for selectable marker genes (resistances to antibiotics) or RNA coding for any cell function desired, such as dihydropholate reductase, thymidine kinase, the maturation enzymes polygalacturonase, pectinesterase etc., proteins responsible for differentiation and development or hormone receptors. In particular types of viruses damaging to plants can advantageously be combatted using the ribozyme-antisense system according to the invention. For this purpose, for example, the procedure as described in the following is carried out. The ribozyme antisense RNA which is directed against other substrates is also synthesized in an analogous procedure.

The DNA oligonucleotides coding for the multifunctional RNA can be prepared synthetically. The oligonucleotides for the antisense RNA can be synthesized on the basis of the viral DNA and RNA sequences. For this any plant-damaging virus can be used in principle. Preferred types of viruses are pathogenic RNA viruses, in particular Cucumber Mosaic Virus, Alfalfa Mosaic Virus, Brome Mosaic Virus, Tobacco Mosaic Virus, Potato Virus X or Y, Tomato Ringspot Virus, Tomato Aspermy Virus or Tobacco Rattle Virus.

At least 10 consecutive nucleotides, in particular 14 to 20 nucleotides, advantageously from the middle of the RNA sequence of the respective virus are preferred as template for the synthesis of the oligonucleotides encoding the ribozyme RNA. This RNA sequence can be both the genome of RNA viruses and an RNA sequence which has been derived from the DNA sequence of a DNA virus. It is particularly advantageous to use the 3 RNA sequences RNA1, RNA2 and RNA3 of the Cucumber Mosaic Virus or parts thereof as a basis, corresponding to the sequences from the publications by Rezaian M. et al., Eur. J. Biochem. 150, 331–339 (1985); Eur. J. Biochem. 143, 277–284 (1984) and Gould I. et al., Eur. J. Biochem. 126, 217–226 (1982).

Figure 1:
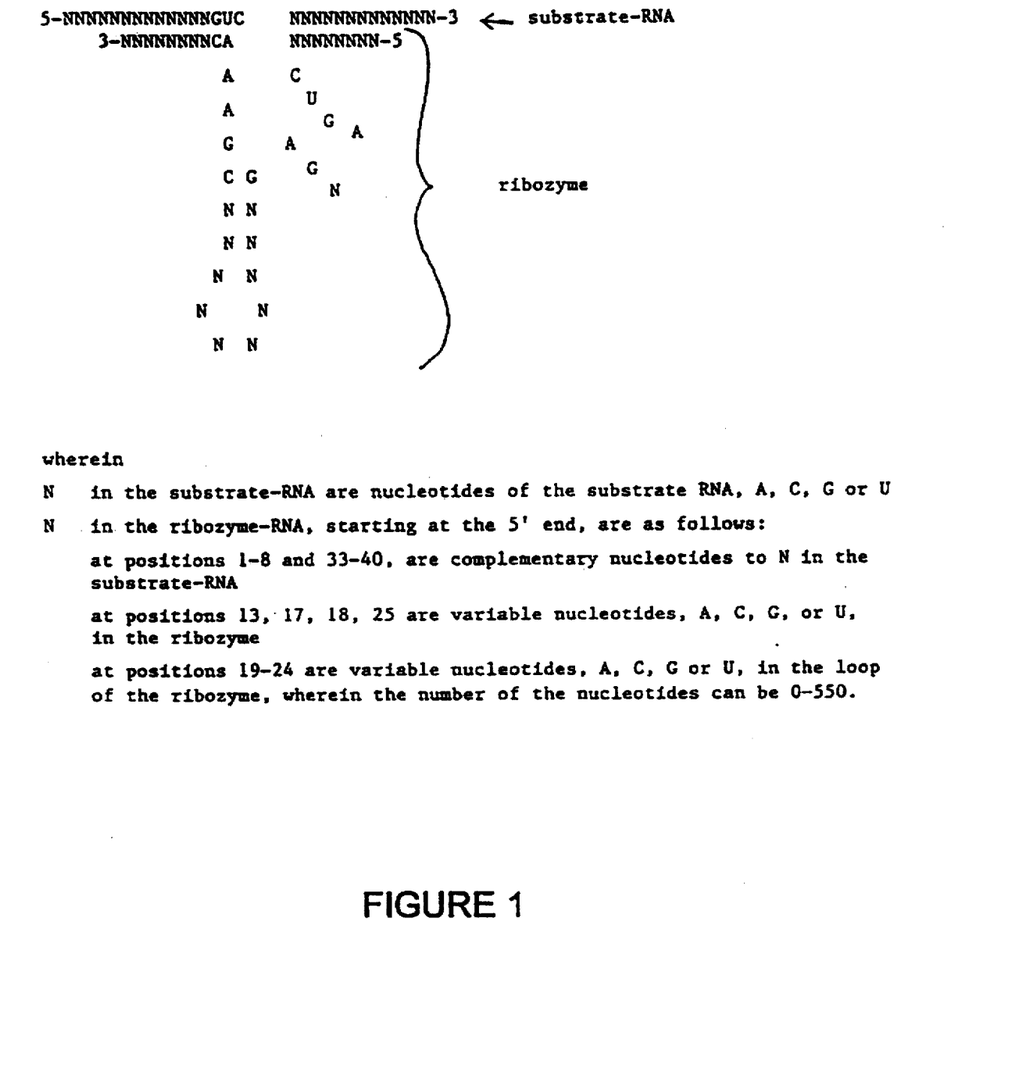
FIG. 1 is a diagram of the ribozyme (SEQUENCE ID NO 4) hybridized with substrate RNA (SEQUENCE ID NO 3).

The oligonucleotides encoding ribozyme are synthesized such that the sequences at the beginning and the end, each consisting of at least 5 nucleotides, preferably 7 to 10 nucleotides are complementary to the RNA of the virus to be inhibited. One part of the sequence lying in between consists of specific nucleotides predetermined for the functionality of the ribozyme and one part consists of variable nucleotides. A diagram of the ribozyme hybridized with substrate RNA can look as in FIG. 1.

The preparation of the antisense RNA is carried out correspondingly but the oligonucleotides are synthesized in such a way that they encode an RNA in the corresponding antisense orientation.

However, the basis for the oligonucleotide synthesis for the ribozyme RNA can also be any substrate desired. In principle, care has only to be taken that the spacer is a substrate for the ribozyme and is provided with the appropriate ribozyme cleavage sites. The spacers for the coupling of the ribozyme and antisense molecules are constructed such that the entire correspondingly expressed RNA, or parts thereof, is complementary to the ribozyme, the complementary nucleotides advantageously grouping around a GUC cleavage site for the ribozyme.

The constructed oligonucleotides are provided with an appropriate linker. Linkers of this type, for example, have cleavage sites of EcoRI, SalI, BamHI, HindIII, EcoRV, SmaI, XhoI, KpnI, preferably XbaI or PstI.

The assembled oligonucleotides are cloned with the aid of the vectors pUC19, pUC18 or pBluescript (Stratagene, Heidelberg, Product Information) and sequenced.

The confirmed oligonucleotide is cloned in an intermediary vector with a plant promoter. Vectors of this type are, for example, the plasmids pPCV701 (Velten J. et al. EMBO J. 3, 2723–2730 (1984)), pNCN (From M. et al. PNAS 82, 5824–5826 (1985)) or pNOS (An G. et al., EMBO J. 4, 277–276 (1985)). The vector pDH51 (Pietrzak, M. et al., NAR 14, 5857, (1986)) with a 35S promoter is preferably used.

After subsequent transformation of E. coli, such as for example E. coli MC 1061, DH1, DK1, GM48 or XL-1, positive clones are identified by methods known per se (Maniatis et al., Lab. Manual), such as plasmid minipreparation and cleavage with an appropriate restriction enzyme.

These positive clones are then subcloned in a binary plant vector, pGV3850 (Zambrysky, P. et al. EMBO J. 2, 2143–2150 (1983)) or pOCA18 (Olszewski, N., NAR 16, 10765–10782, (1988)) can be employed as plant vectors. pOCA18 is preferably used.

The resulting binary plant vectors which contain a plant promoter with the attached DNA fragment which is constructed as described above in the T-DNA are used to transform plants. This can be carried out by techniques such as electroporation or microinjection.

The cocultivation of protoplasts or the transformation of small pieces of leaves using agrobacteria is preferably employed. For this purpose the plant vector construct is transferred by transformation with purified DNA or, mediated by a helper strain such as E. coli SM10 (Simon R. et al., Biotechnology 1, 784–791 (1983)), in Agrobacterium tumefaciens, such as A 282, with a Ti plasmid via a triparental mating. Direct transformation and triparental mating were carried out as described in "Plant Molecular Biology Manual" (Kluwer Academic Publishers, Dardrecht (1988)).

Basically all plants can be transformed with the binary plant vectors carrying the constructed DNA according to the invention. Dicotyledonous plants, in particular useful plants which produce or store, for example, starch, carbohydrates, proteins or fats in usable amounts in their organs or produce fruit and vegetables or provide spices, fibers and technically usable products or pharmaceuticals, dyes or waxes are preferred as are fodder plants.

Tomato, strawberry and avocado as well as plants which carry tropical fruit, for example papaya, mango, but also pear, apple, nectarine, apricot or peach shall be mentioned as examples. Furthermore all types of cereal, rape, potatoes, soybean, cotton, corn, sugarbeet or sunflower shall be listed as examples of plants to be transformed. The transformed cells are selected with the aid of a selection medium, grown to a callus and regenerated to the plant on an appropriate medium (Shain et al, Theor. appl. Genet. 72, 770–770 (1986); Masson, J. et al., Plant Science 53, 167–176 (1987); Zhan et al., Plant Mol. Biol. 11, 551–559 (1988); McGranaham et al., Bio/Technology 6, 800–804 (1988); Novrate et al., Bio/Technology 7, 154–159 (1989)).

The resultant plant is changed by the transformation so far as the RNA expressed with the aid of the constructed oligonucleotides is cleaved on GUC cleavage sites by the ribozyme activity in the cells and antisense RNA is released for this reason, it being possible for ribozyme RNA together with antisense RNA to become active towards virus DNA or RNA.

The examples which follow serve to illustrate the invention further.

EXAMPLES

Percentages relate to weight if not specified otherwise.
Synthesis of the DNA for the expression of the multifunctional RNA
The synthesis of the DNA sequence of Table 1 for the expression of the multifunctional RNA was carried out as described below:
  a) Ribozyme I [1–46]: the regions homologous to CMV are based on the published RNA 1 sequence (Rezaian M. et al., Eur. J. Biochem. 150, 331–339 (1985)) from position 3248 to 3264. The constant regions for the ribozyme can be seen in Table 1 and were derived from the publication by Haseloff, J. et al., Nature 334, 585–591 (1988).
  b) Spacer [47–70]: based on the published RNA 2 sequence (Rezaian, M. et al., Eur. J., Biochem. 143, 277–284 (1984)) from position 2853 to 2870.

c) Antisense 1 [71–219]: based on the published RNA 4 sequence (Gould I. et al., Eur. J. Biochem. 143, 217–226 (1982)) from position 2054 to 2193.

d) Spacer [219–243]: as for spacer [47–70] under b.

e) Antisense 2 [244–313]: based on the published RNA 2 sequence (see above) from position 71 to 134.

f) Spacer [314–338]: as for spacer [47–70] under b.

g) Antisense 3 [339–405]: based on the published RNA 4 sequence (see above) from position 1200 to 1261.

h) Spacer [406–429]: based on the published RNA 1 sequence (see above) from position 3248 to 3264.

i) Ribozyme [430–480]: for the regions homologous to CMV based on the RNA 2 sequence (see above) from position 2853 to 2870; for the constant regions according to Table 1 see publication under a).

The square brackets relate to the positions of the attached DNA sequence for the expression of the multifunctional RNA (Table 1).

With the aid of the phosphoramide method, the oligonucleotides listed in Table 1 were synthesized using a synthesizer. The fragments can be seen from the sequence. The first one extends from the XmaI linker at the start to the KpnI side, the second one from KpnI to BamHI, the third one from BamHI to SacI and the fourth one from SacI to the SmaI junction at the end. Strand and complementary strand were synthesized in each case, which were combined in equimolar amounts before the cloning.

2. Cloning in pBluescript SK+ and sequencing

The plasmid pBluescript SK+ (stratagene, product information) was opened with the particular enzymes (XmaI/KpnI, KpnI/BamHI, BamHI/SacI, SacI/SmaI) and, after treatment with calf intestinal phosphatase (CIP), ligated with a fivefold excess of the double stranded phosphorylated oligonucleotide. After induction by isopropylthiogalactoside (IPTG, Boehringer Mannheim), it was possible to identify positive clones as white colonies in the strain XL-Blue (stratagene) on LB-plates containing 5-bromo-4-chloro-3-indolyl-β-D-galactoside (X-gal) (Boehringer, Mannheim).

5 of the colonies were isolated in each case and sequenced by the dideoxy termination method (Boehringer, Sequencing Kit). After cleaving with the appropriate enzymes, the oligonucleotide was isolated from a colony with the expected sequence from a highly pure (low melt) agarose gel (Gibco, Brueggenstein, FR Germany).

The isolated oligonucleotides were ligated and separated from nonligated ones on a highly pure (low melt) agarose gel. The expected 0.5 kb band was cut out and, after filling the overhanging XmaI site, inserted into the SmaI recognition sequence of pBluescript SK+.

Figure 2:
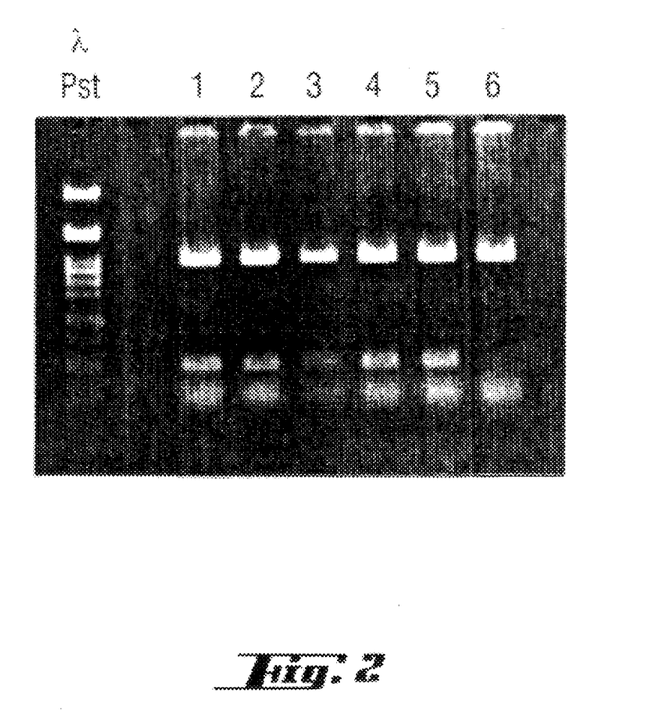
FIG. 2 is a photograph showing 6 colonies of a plasmid preparation from L-1 Blue cells which were transformed with the vector pBluescript into which the complete fragment has been incorporated.

The photograph in FIG. 2 shows 6 colonies of a plasmid preparation from XL-1 Blue cells which were transformed with the vector pBluescript into which the complete fragment has been incorporated. The plasmids were cut with SmaI before the application onto the gel. In colonies 1–5 a fragment of the expected size can be detected.

3. Cloning of the entire fragment into pDH51

The fragment for the expression of the multifunctional RNA was isolated from the pBluescript construction by digestion with SmaI and was incorporated into an SmaI-cut pDH51. It was possible to determine the orientation of the fragment by HindIII.

The plasmid pDH51 is reproducibly described in Pietrzak, M. et al., NAR 14, 5857–5869 (1986).

Figure 3:
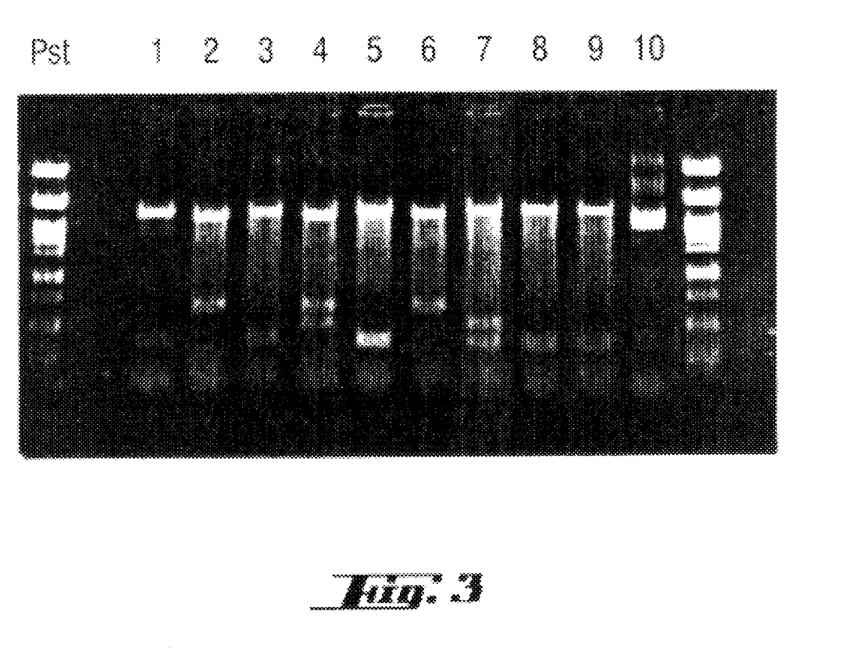
FIG. 3 shows DNA minipreparations of MC1061 cells after transformation with pDH51 into which the multifunctional DNA fragment was incorporated into the SmaI site.

FIG. 3 shows DNA minipreparations of MC1061 cells after transformation with pDH51 into which the multifunctional DNA fragment was incorporated into the SmaI site.

The DNA minipreparations were HindIII-cleaved. An incorporation having the desired orientation appears in the preparations 1, 3, 5, 8 and 9.

4. Cloning of the entire fragment with 35S promoter into pOCA18

The 1.2 kb fragment for the expression of the multifunctional RNA was isolated together with the 35S promoter and terminator by an EcoRI-digestion of the pDH51 containing the cloned insert. The isolated fragment was ligated with an EcoRI-cut pOCA18 vector. The vector ligated with the fragment was transferred into MC1061 cells by transformation. The plasmid pOCA18 is reproducibly described in Olszewski, N. et al. NAR 16, 10765–10782 (1988).

Figure 4:
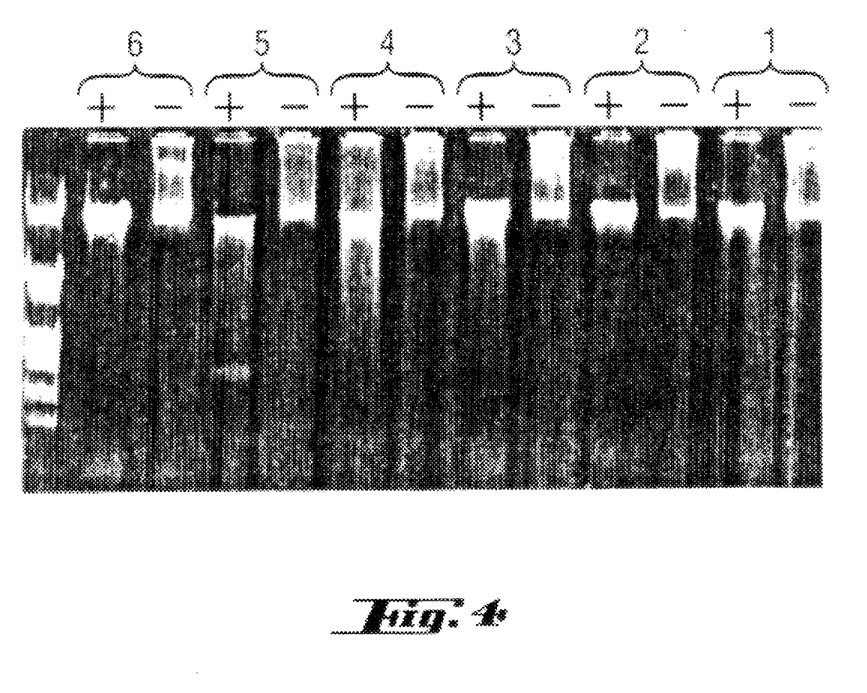
FIG. 4 shows DNA minipreparations from MC1061 cells which were transformed with pOCA18 into which the EcoRI fragment was ligated.

FIG. 4 shows DNA minipreparations from MC1061 cells which were transformed with pOCA18 into which the EcoRI fragment was ligated. The DNA was cleaved with EcoRI (designated "+") before applying it onto the gel. In addition, the same amount of uncleaved DNA was applied in-each case ("−"). The colony 5 from this experiment resulted in an EcoRI band of the desired size.

5. Transformation of agrobacteria

The vector pOCA18 containing the 35S promoter/oligonucleotide insert was transferred into the agrobacteria strain A 282 (Pharmacia, Freiburg, FR Germany, or ATCC 37349, USA). This was effected by a triparental mating with the aid of the E. coli strain SM10 (Simon, R. et al. Bio/Technology 1, 784–791, 1983). For this purpose equal amounts of the bacteria were placed together on a filter overnight, the filter was rinsed with 2 ml of 10 mM $MgSO_4$ and aliquots thereof were placed on YEB plates containing tetracyclin and rifampicin (YEB: 1% yeast extract, 1% peptone, 0.5% NaCl). It was possible to detect positive agrobacteria by hybridization. For this purpose the colonies are transferred onto Gene Screen Plus filters (New England Nuclear, Boston). The filters were incubated at 28° C. on YEB plates overnight, and denatured and neutralized on the next day. Subsequently the filters were hybridized with $4 \times 10^5$ cpm/nl of the radiolabeled entire fragment at 65° C. overnight.

The filters were washed at 65° C. 1× with 1×SSC and 2× with 0.1×SSC/SDS for 30 minutes in each case.

Figure 5:
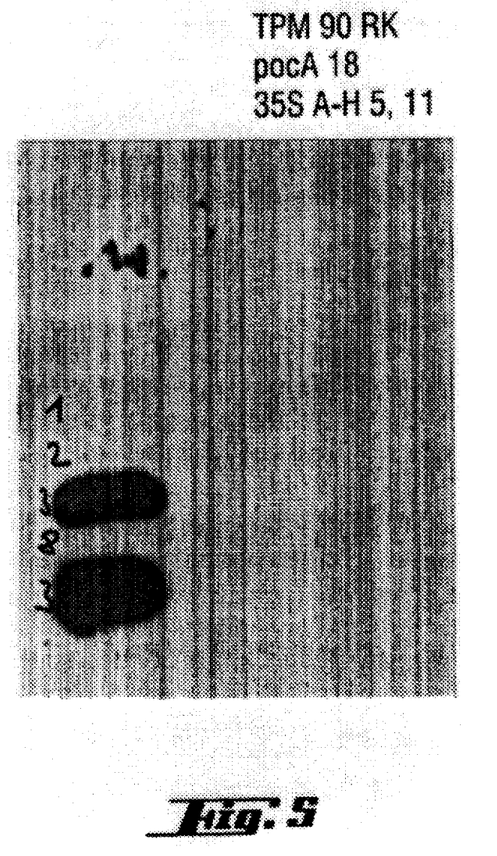
FIG. 5 shows a film which was exposed on the washed filters for 6 hours to confirm the result in Example 5.

FIG. 5 shows a film which was exposed on the washed filters for 6 hours. The colony 3 is positive. The latter was applied in duplicate in order to confirm the result of a preceding experiment.

6. Transformation of tobacco

The agrobacteria were grown in YEB medium (1% yeast extract, 1% peptone, 0.5% NaCl) containing tetracyclin and rifampicin, 20 ml of the bacteria were centrifuged off, washed once in YEB medium and, suspended in 20 ml of 10 mM $MgSO_4$, placed in a Petri dish. Nicotiana tabacum, Wisconsin 38 was used as plant material. The plants had been cultivated for 4 weeks under sterile conditions on 2 MS medium (Murashige T. et al., Physiol. Plant 15, 473–497 (1962)) at 25° C. with 16 h of light per day. A 1 $cm^2$ piece of leaf was cut off from these plants, injured with sterile emery paper and immersed in the bacteria culture for 30 s. The pieces of leaf were maintained on MS medium, as described above for 2 MS, at 25° C. for 2 days and then washed using liquid 2 MS medium. The pieces of leaf were then placed on MSC 10 (as MS containing 1.5% agar) plates containing kanamycin. After 5–6 weeks it was possible to replant regenerated plants in larger vessels where they formed roots after 2–3 weeks.

DNA was isolated from transgenic tobacco plants by the CTAB method. The protocol of the "Plant Molecular Biology Manual", Kluwer Academic Publishers, Dordrecht (1988) was strictly followed in this connection. 10 µg of the DNA were cleaved with EcoRI, separated on a 1% agarose gel and, after denaturing, transferred onto a Gene Screen Plus membrane. The membrane was hybridized with 4×10$^5$ cpm/ml of the radiolabeled fragment at 65° C. overnight. It was possible in all cases to detect a fragment of the expected size.

Figure 6:
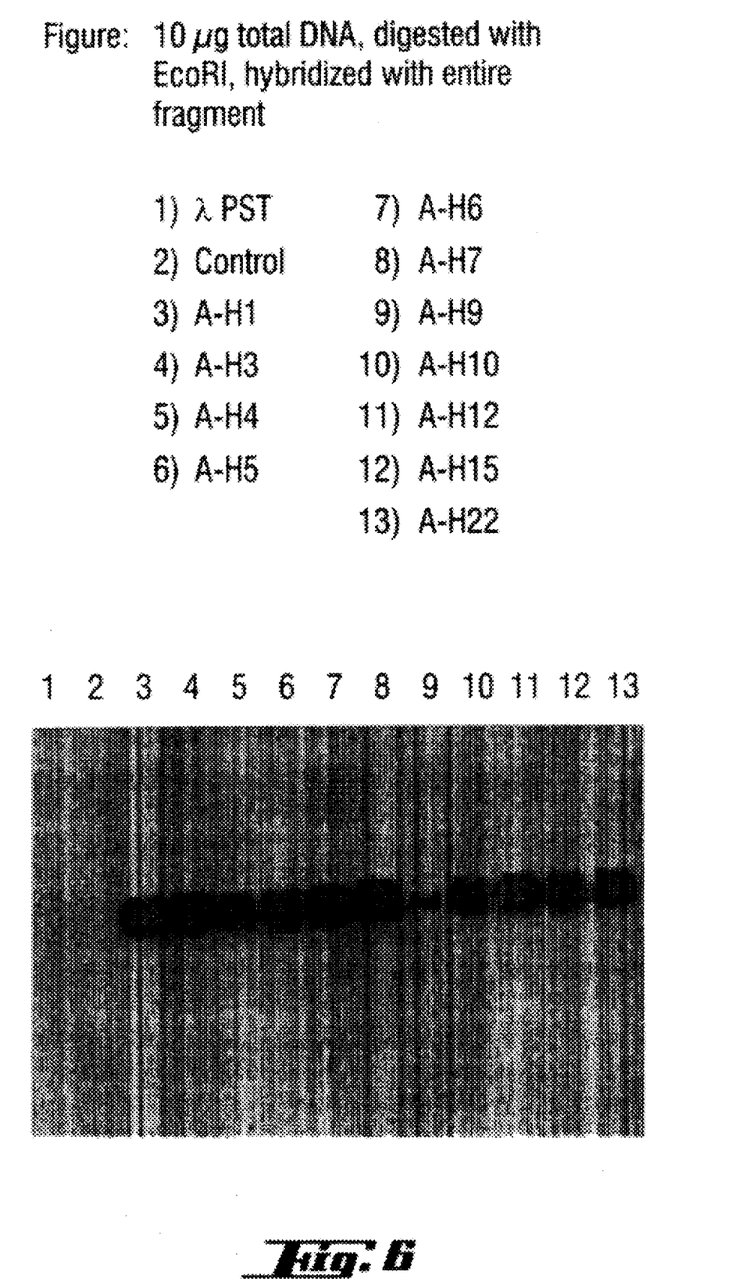
FIG. 6 shows the DNA preparations from transgenic plants discussed in Example 6.

All DNA preparations from transgenic plants show the expected hybridization as a 1.2 kb EcoRI band. (See FIG. 6.)

7. Expression of the multifunctional RNA using transgenic tobacco plants

Total RNA was isolated from pieces of leaf of transgenic tobacco plants. The protocol of the "Plant Molecular Biology Manual", Kluwer Academic Publishers, Dordrecht (1988) was followed in this connection. After denaturing, 10 µg of the total RNA were fractionated on a 2.2M formaldehyde/1% agarose gel in 12 mM tris pH 7.5/0.1 mM EDTA buffer and transferred onto a Gene Screen Plus membrane. The membrane was hybridized with radiolabeled entire fragment.

The transgenic plants show a strong RNA expression with the expected specificity.

8. Infection of transgenic tobacco plants with CMV

Infection was carried out with the CMV strain Q (Rezaian, M. et al., Eur. J. Biochem. 150, 331 (1985); 143, 277 (1984); Gould, J. et al., Eur. J. Biochem. 126, 217 (1982)) which was obtained from cucumber leaves. The infectious particles were applied to the tobacco plants with the aid of carborundum. Under the selected infection conditions, 80% of the control plants showed severe symptoms which consisted of brightening of the veins, formations of mosaics and irregular growth of the leaf edges. It was possible to confirm specificity of the infection by ELISA.

The test of the transgenicity was carried out on plants which had previously been propagated by cuttings. A confirmation on the progeny was carried out if seeds were present.

It has been found that a strong reduction in the probability of infection had occurred practically in all plants which showed an expression of the multifunctional RNA. Only about 10–50% of the transgenic plants, depending on a specific event of transformation in each case, developed the typical symptoms of infection.

TABLE

| Percentages of infected plants having significant symptoms; 10 plants were evaluated in each case | | |
|---|---|---|
| | 12 days | 20 days |
| Control | | |
| Tobacco W38 | 80 | 80 |
| Transgenes: | | |
| A-H3 | 20 | 30 |
| A-H7 | 10 | 20 |
| A-H15 | 40 | 50 |
| A-H22 | 30 | 30 |

Thus the method used proved to be suitable for protecting plants from viral infections. In order to improve the resistance, it can be attempted to attach even more elements to the multifunctional RNA.

Sequence for the expression of a multifunctional RNA

TABLE 1

```
XmaI
                9          18         27         36
5' CCG GGA GGT AGC TCC TGA TGA GTC CGT GAG GAC GAA ACA ACC
3'   C CCT CCA TCG AGG ACT ACT CAG GCA CTC CTG CTT TGT TGG 45         54         63         72         81
    TTG TCG TCG ACA AAA TGG TCA GTA TGC CCC TCG AGT GGT CTC
    ACC AGC AGC TGT TTT ACC AGT CAT ACG GGG AGC TCA CCA GAG 90         99        108        117  KpnI    126
    CTT ATG GAG AAC CTG TGG AAA ACC ACA GGC GGT ACC CGC ACT
    GAA TAC CTC TTG GAC ACC TTT TGG TGT CCG CCA TGG GCG TGA 135        144        153        162
    CTT GGT AAT ATC AGT GTA TTA CCG TGC ACG AGC TTC TCA CGA
    GAA CCA TTA TAG TCA CAT AAT GGC ACG TGC TCG AAG AGT GCT 171        180        189        198        207
    AGC CCT TCC GAA GAA ATC TAG GAG ATG ATT TCA AGG GTA GCT
    TCG GGA AGG CTT CTT TAG ATC CTC TAC TAA AGT TCC CAT CGA

216  BamHI 225        234        243        252
    CGA CAA CCT GGA TCC AAA ATG GTC AGT ATG CCC CCC ATG GCA
    GCT GTT GGA CCT AGG TTT TAC CAG TCA TAC GGG GGG TAC CGT 261        270        279        288
    ACA GAT TGG CGA ATG AGA AAG TGG GTG GAG GAC TTA TCA TAG
    TGT CTA ACC GCT TAC TCT TTC ACC CAC CTC CTG AAT AGT ATC 297        306        315        324        333
    TAA CAG AAG AGA GAC TAG AAC TGC AGA AAA TGG TCA GTA TGC
    ATT GTC TTC TCT CTG ATC TTG ACG TCT TTT ACC AGT CAT ACG 342        351        360        369   SacI 378
    CCC AGA TCT ACC GGA GGT TCT ACT AGC ATT GGG AGA GCT CGA
    GGG TCT AGA TGG CCT CCA AGA TGA TCG TAA CCC TCT CGA GTC
```

TABLE 1-continued

```
      387         396         405         414
TTT GTC CAT AGG CAC ACT GAG ACG CAA AAA GCT TAA GGT TGT
AAA CAG GTA TCC GTG TGA CTC TGC GTT TTT CGA ATT CCA ACA 423         432         441         450         459
CGA GCT ACC GGG GCC CAG GGC ATA CTC TGA TGA GTC CGT GAG
GCT CGA TGG CCC CGG GTC CCG TAT GAG ACT ACT CAG GCA CTC 468         477 Sma
GAC GAA ACC ATT TTG GG 3'   SEQUENCE ID NO. 1
CTG CTT TGG TAA AAC CC 5'   SEQUENCE ID NO. 2
```

---

We claim:

1. An isolated DNA fragment which encodes a pattern which comprises:

5'-hammerhead ribozyme RNA-(spacer-antisense RNA)$_n$-spacer-hammerhead ribozyme RNA-3', wherein n is a number from 0 to 10, and the spacer is a chain of 20 to 25 nucleotides which contains a ribozyme cleavage site in each case; and wherein said DNA fragment encodes a multifunctional RNA with self-processing activity.

2. The isolated DNA fragment as claimed in claim 1, wherein the encoded antisense RNA is complementary to a viral RNA.

3. The isolated DNA fragment as claimed in claim 1, wherein the encoded ribozyme mRNA has at least 6 consecutive nucleotides at each of the 5' and 3' ends that are complementary to a viral RNA.

4. The isolated DNA fragment which comprises the DNA SEQUENCE ID NO. 1.

5. A multifunctional RNA encoded by the isolated DNA fragment as claimed in claim 1.

6. A plant host cell containing the DNA fragment as claimed in claim 1.

7. A plant host cell containing an RNA as claimed in claim 5.

8. The plant host cell of claim 6, wherein said plant host cell is a dicotyledonous plant host cell.

9. The plant host cell of claim 7, wherein said plant host cell is a dicotyledonous plant host cell.

10. A multifunctional RNA as claimed in claim 6, wherein the RNA is encoded by the isolated DNA fragment comprising the sequence in SEQUENCE ID NO. 1.

\* \* \* \* \*

UNITED STATES PATENT AND TRADEMARK OFFICE
CERTIFICATE OF CORRECTION

PATENT NO. : 5,707,840
DATED : January 13, 1998
INVENTOR(S) : Hubert MULLNER et al.

It is certified that error appears in the above-indentified patent and that said Letters Patent is hereby corrected as shown below:

Title Page, Item [75], in the Inventors, line 4, after "Kelkheim;", insert --all of Germany;--; and line 5, "all of Germany" should read --Netherlands--.

Claim 1 column 11, line 47, after "ribozyme", insert --RNA-spacer-antisense--.

Claim 2, column 11, line 55, "vital" should read --viral--.

Signed and Sealed this

Second Day of June, 1998

Attest:

BRUCE LEHMAN

*Attesting Officer*  *Commissioner of Patents and Trademarks*